United States Patent [19]

Roeser et al.

[11] Patent Number: 4,639,447
[45] Date of Patent: Jan. 27, 1987

[54] AZOLYLNITRILES, AND FUNGICIDES CONTAINING THESE COMPOUNDS

[75] Inventors: Karl Roeser, Hirschberg; Manfred Lauer, Ludwigshafen; Hubert Sauter, Mannheim; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 741,112

[22] Filed: Jun. 4, 1985

[30] Foreign Application Priority Data

Jun. 7, 1984 [DE] Fed. Rep. of Germany ....... 3421179

[51] Int. Cl.$^4$ .................. A01N 43/50; A01N 43/653; C07D 233/61; C07D 249/08
[52] U.S. Cl. ..................................... 514/222; 514/228; 514/230; 514/232; 514/237; 514/252; 514/256; 514/318; 514/326; 514/332; 514/333; 514/357; 514/365; 514/383; 514/397; 514/399; 544/58.2; 544/58.5; 544/58.6; 544/60; 544/122; 544/124; 544/132; 544/133; 544/139; 544/295; 544/333; 544/360
[58] Field of Search ............... 544/58.2, 58.5, 58.6, 544/60, 122, 124, 132, 133, 139, 295, 333, 360, 364, 366, 369, 370; 546/193, 194, 209, 210, 256, 264, 276, 278, 280, 281, 283, 284, 330; 548/205, 262, 336, 341; 514/222, 228, 230, 232, 237, 252, 236, 318, 326, 332, 333, 357, 365, 383, 397, 399

[56] References Cited

U.S. PATENT DOCUMENTS

4,584,008  4/1986  Cherpeck .................. 548/262 X

FOREIGN PATENT DOCUMENTS

1318590  5/1973  United Kingdom .

OTHER PUBLICATIONS

Bencze et al., Chemical Abstracts, vol. 58 (1963) 13911a.
Bencze, Chemical Abstracts, vol. 59 (1963) 11449d.
Kato et al., Chemical Abstracts, vol. 70 (1969) 106329z.
Ten Haken et al., Chemical Abstracts, vol. 101 (1984) 23355n.

*Primary Examiner*—Richard L. Raymond
*Attorney, Agent, or Firm*—Keil & Weinkauf

[57] ABSTRACT

Compounds of the formula

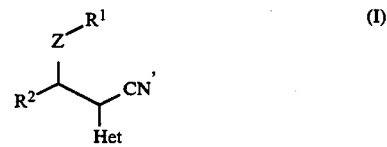

where $R^2$ is a 5-membered or 6-membered heterocyclic structure possessing one or two hetero atoms or is phenyl which is unsubstituted or substituted by $R_n$, R is hydrogen, alkyl, alkoxy, alkylthio, alkylsulfonyl, halogen, haloalkyl, nitro, cyano, unsubstituted or substituted phenyl, unsubstituted or substituted phenoxy or unsubstituted or substituted amino, $R^1$ is alkyl, cycloalkyl, cycloalkylalkyl, unsubstituted or substituted aryl, unsubstituted or substituted aralkyl, unsubstituted or substituted aryloxyalkyl, unsubstituted or substituted benzyloxyalkyl, unsubstituted or substituted alkenyl, unsubstituted or substituted alkynyl or $(CH_2-CH_2O)_m-R^4$, where $R^4$ is $C_1-C_4$-alkyl, unsubstituted or substituted aryl or unsubstituted or substituted benzyl and m is 1, 2, 3 or 4, Het is 1,2,4-triazol-1-yl, imidazol-1-yl or pyrid-3-yl, n is 1, 2, 3, 4 or 5, Z is $CH_2$, oxygen, $SO_t$ or ($R^3$N), where t is 0, 1 or 2 and $R^3$ has the same meanings as $R^1$ and is identical to or different from $R^1$ or together with $R^1$ forms a diradical of the formula $-(CH_2)_k-X-(CH_2)_l-$, where k and l independently of one another are each 1, 2, 3, 4 or 5, and X is O, S or NH, or $Z-R^1$ is unsubstituted or substituted phenyl, and their plant-tolerated acid addition salts, and fungicides containing them.

4 Claims, No Drawings

AZOLYLNITRILES, AND FUNGICIDES CONTAINING THESE COMPOUNDS

The present invention relates to useful novel azolylnitriles and to fungicides containing these compounds.

It has been disclosed that azole compounds, eg. 1-[2-(2,4-dichlorophenyl)-2-(2-propenyloxy)-ethyl]-1H-imidazole, can be used as fungicides (GB-1,318,590). However, the action of these compounds is unsatisfactory.

We have found novel compounds of the formula I

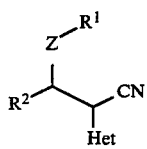

where $R^2$ is a 5-membered or 6-membered heterocyclic structure possessing one or two hetero atoms or is phenyl which is unsubstituted or substituted by $R_n$, R is hydrogen, alkyl, alkoxy, alkylthio, alkylsulfonyl, halogen, haloalkyl, nitro, cyano, unsubstituted or substituted phenyl, unsubstituted or substituted phenoxy or unsubstituted or substituted amino, $R^1$ is alkyl, cycloalkyl, cycloalkylalkyl, unsubstituted or substituted aryl, unsubstituted or substituted aralkyl, unsubstituted or substituted aryloxyalkyl, unsubstituted or substituted benzyloxyalkyl, unsubstituted or substituted alkenyl, unsubstituted or substituted alkynyl or $(CH_2-CH_2O)_m-R^4$, where $R^4$ is $C_1-C_4$-alkyl, unsubstituted or substituted aryl or unsubstituted or substituted benzyl and m is 1, 2, 3 or 4, Het is 1,2,4-triazol-1-yl, imidazol-1-yl or pyrid-3-yl, n is 1, 2, 3, 4, or 5, Z is $CH_2$, oxygen, $SO_t$ or $(R^3N)$, where t is 0, 1 or 2 and $R^3$ has the same meanings as $R^1$ and is identical to or different from $R^1$ or together with $R^1$ forms a diradical of the formula $-(CH_2)_k-X-(CH_2)_L-$, where k and l independently of one another are each 1, 2, 3, 4 or 5, and X is O, S or NH, or $Z-R^1$ is unsubstituted or substituted phenyl, and their plant-tolerated acid addition salts, which have a better fungicidal action than the known compound.

In formula I, $R^2$ is, for example, an unsaturated heterocyclic radical, which contains, for example, 2 or 3 double bonds in the heterocyclic structure and 1 or 2 atoms from the group consisting of oxygen, sulfur and nitrogen, and a total of 5 or 6 ring members, eg. thienyl, pyridyl, furyl, pyrimidyl or thiazolyl, preferably thien-2-yl, thien-3-yl, pyrid-3-yl, pyrid-4-yl and fur-2-yl, for example thien-3-yl, pyrid-3-yl or fur-2-yl.

$R^2$ may furthermore be phenyl which is unsubstituted or substituted by $R_n$. R is, for example, halogen (fluorine, chlorine, bromine or iodine), nitro, cyano, alkyl of 1 to 4 carbon atoms, eg. methyl, ethyl, n-propyl, isopropyl, cyclopropyl, n-butyl, isobutyl, sec.-butyl, tert.-butyl or cyclobutyl, $C_1-C_4$-alkylsulfonyl, eg. methylsulfonyl, ethylsulfonyl, n-propylsulfonyl or n-butylsulfonyl, alkoxy of 1 or 2 carbon atoms (methoxy or ethoxy), alkylthio of 1 or 2 carbon atoms, haloalkyl of 1 to 4, in particular 1 or 2, carbon atoms and 1 to 5 halogen atoms, in particular 1 to 3 identical or different halogen atoms, preferred halogen atoms being fluorine or chlorine, and an example of haloalkyl being trifluoromethyl.

R may furthermore be phenyl or phenoxy, each of which is unsubstituted or monosubstituted or polysubstituted (disubstituted or trisubstituted) by identical or different substituents, preferred substituents in each case being halogen, in particular fluorine, chlorine or bromine, cyano, nitro or haloalkyl of 1 or 2 carbon atoms and 1 to 3 identical or different halogen atoms, preferred halogen atoms being fluorine or chlorine and an example of haloalkyl being trifluoromethyl.

Unsubstituted or substituted amino is, for example, amino, $C_1-C_4$-alkylamino or $C_1-C_4$-dialkylamino.

$R^1$ is, for example, alkyl of 1 to 10 carbon atoms, eg. methyl, ethyl, n-propyl, isopropyl, sec.-butyl, neopentyl, n-hexyl, n-heptyl, n-octyl, n-nonyl or n-decyl, or $C_3-C_8$-cycloalkyl, eg. cyclopropyl, cyclobutyl, cyclopentyl, cyclohexyl, cycloheptyl or cyclooctyl, in particular cyclopropyl, cyclopentyl or cyclohexyl.

Other advantageous compounds are those in which $R^1$ is cycloalkylalkyl having a total of 4 to 11 carbon atoms, eg. cyclopropylmethyl, cyclobutylmethyl, cyclopentylmethyl, cyclohexylmethyl, cyloheptylmethyl, cyclopropylethyl, cyclobutylethyl, cyclopentylethyl or cyclohexylethyl.

$R^1$ may furthermore be unsubstituted or substituted phenyl or unsubstituted or substituted phenylalkyl (eg. benzyl), and the substituents may be halogen (in this case preferably fluorine or chlorine), cyano, nitro, $C_1-C_4$-alkyl, $C_1-C_4$-alkoxy, $C_1-C_4$-alkylthio or haloalkyl of 1 to 4 carbon atoms and 1 to 9 halogen atoms, for example benzyl, 4-chlorobenzyl or 2,4-dichlorobenzyl.

$R^1$ may furthermore be, for example, unsubstituted or substituted phenoxyalkyl or unsubstituted or substituted benzyloxyalkyl where alkyl is of 2 to 10 carbon atoms and the phenyl ring has not more than 5 identical or different substituents, which may be halogen (in this case preferably fluorine or chlorine), cyano, nitro, $C_1-C_4$-alkyl, $C_1-C_4$-alkoxy, $C_1-C_4$-alkylthio or haloalkyl of 1 to 4 carbon atoms and 1 to 9 halogen atoms.

Examples are phenoxyethyl, phenoxypropyl, phenoxybutyl, phenoxypentyl, phenoxyhexyl, phenoxyheptyl, phenoxyoctyl, phenoxynonyl, phenoxydecyl, p-chlorophenoxyethyl, p-chlorophenoxypropyl, p-chlorophenoxybutyl, 2,4-dichlorophenoxyethyl, 2,4-dichlorophenoxypropyl, 2,4-dichlorophenoxybutyl, benzyloxyethyl, benzyloxypropyl, benzyloxybutyl, benzyloxypentyl, benzyloxyhexyl, benzyloxyheptyl, benzyloxyoctyl, benzyloxynonyl and benzyloxydecyl. Alkenyl is, for example, $C_2-C_4$-alkenyl(allyl), and alkynyl is, for example, propargyl or butynyl.

$R_1$ may furthermore be a radical of the formula $-(CH_2CH_2O)_m-R^4$, where m is an integer from 1 to 4 and $R^4$ is alkyl of 1 to 4 carbon atoms, unsubstituted or substituted phenyl or unsubstituted or substituted benzyl. Examples are $-CH_2-CH_2-O-CH_3$, $-CH_2-CH_2-O-C_3H_7$, $CH_2-CH_2-O-C_4H_9$, $CH_2-CH_2-O-CH_2-CH_2-O-CH_3$, $CH_2-CH_2-O-CH_2-CH_2-O-C_2H_5$, $CH_2-CH_2-O-CH_2-CH_2-O-C_3H_7$, $CH_2-CH_2-O-CH_2-CH_2-O-C_4H_9$, $CH_2-CH_2-O-C_6H_5$,

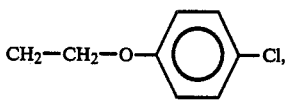

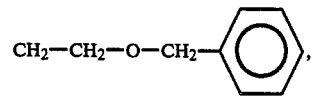

-continued

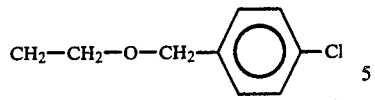

In formula I, Z is CH$_2$, oxygen or SO$_t$, for example —S—, SO or SO$_2$. Z may furthermore be R$^3$N, where R$^3$ is selected from the same group of substituents as R$^1$ and is identical to or different from R$^1$. Furthermore, R$^1$ and R$^3$ together can form a diradical of the formula —(CH$_2$)$_k$—X—(CH$_2$)$_l$—, where k and l independently of one another are each 1, 2, 3, 4 or 5 and X is CH$_2$, oxygen, sulfur or NH. Examples of Z are CH$_3$—N>, C$_2$H$_5$—N>, n—C$_3$H$_7$N>, i—C$_3$H$_7$N>, phenyl—CH$_2$N> and phenyl—N>, and examples of —Z—R$^1$ are

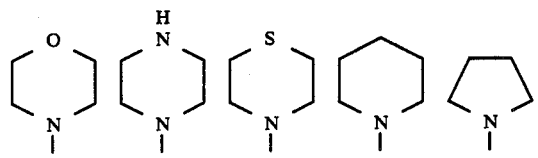

Z—R$^1$ may furthermore be phenyl which is unsubstituted or substituted by R$_n$ and in which R and n have the above meanings, particularly suitable substituents R$_n$ being the halogens, and examples being 2—F—phenyl, 3—F—phenyl, 4—F—phenyl, 2—Cl—phenyl, 3—Cl—phenyl, 4—Cl—phenyl and 2,4—Cl$_2$—phenyl.

Examples of plant-tolerated salts of the compounds are the sulfates, bisulfates, nitrates, hydrochlorides, hydrobromides, p-toluenesulfonates and oxalates.

In formula III, M is a monovalent, divalent, trivalent or tetravalent metal, in particular Li, Na, K, Mg, Ca, Al, Zr and Ti, for example Li or Mg.

M may furthermore be a metal complex, in particular a copper complex, for example a complex of the formula [CuCH$_2$R$^1$]Li, where R$^1$ has the above meanings, or a complex of the formula [CuR$^5$]Li, where R$^5$ is alkynyl. Examples of such complexes are [(CH$_3$)$_2$Cu]Li, [(C$_2$H$_5$)$_2$Cu]Li, [(n—C$_3$H$_7$)$_2$Cu]Li, [(n—C$_4$H$_9$)$_2$Cu]Li, [(n—C$_5$H$_{11}$)$_2$Cu]Li, [(n—C$_6$H$_{13}$)$_2$Cu]Li, [(n—C$_7$H$_{15}$)$_2$Cu]Li, [(n—C$_8$H$_{17}$)$_2$Cu]Li, [(n—C$_9$H$_{19}$)$_2$Cu]Li, [(n—C$_{10}$H$_{21}$)Cu]Li, [CH$_3$CuC≡C—CH$_3$]Li, [C$_2$H$_5$CuC≡C—CH$_3$]Li, [n—C$_3$H$_7$CuC≡C—CH$_3$]Li, [n—C$_4$H$_9$CuC≡C—CH$_3$]Li, [n—C$_5$H$_{11}$CuC≡C—CH$_3$]Li, [n—C$_6$H$_{13}$CuC≡C—CH$_3$]Li and [n—C$_7$H$_{15}$CuC≡C—CH$_3$]Li The radical of a metal compound is, for example, —MgCl, —CuCl, —CaCl or AlCl$_2$.

The compounds of the formula I can be prepared using one of the schemes listed below:

Scheme A

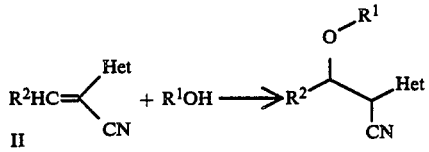

Scheme B

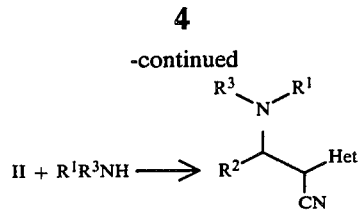

Scheme C

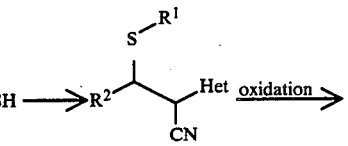

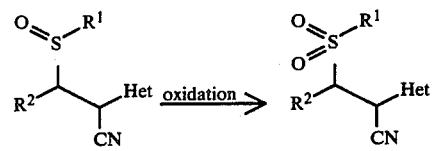

Scheme D

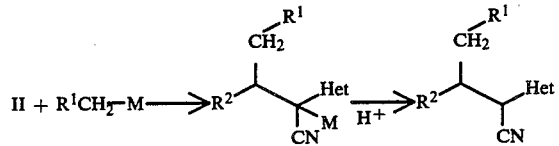

The reactions can be carried out in the presence or absence of a diluent and/or a catalyst. Examples of suitable diluents are diethyl ether, chloroform, methylene chloride, toluene, xylenes, tetrahydrofuran, dioxane, dimethyl sulfoxide, dimethylformamide, methanol, ethanol and tert.-butanol. Examples of advantageous catalysts are amines, eg. triethylamine or diisopropylamine, metal hydroxides, such as sodium hydroxide or potassium hydroxide, metal alcoholates, eg. sodium methylate or potassium tert.-butylate, and ammonium bases, such as Triton B. Other advantageous catalysts are mineral acids, eg. sulfuric acid or hydrochloric acid, organic acids, eg. formic acid, acetic acid or p-toluenesulfonic acid, and acidic or basic, liquid or solid ion exchangers.

The present invention furthermore relates to the intermediates of the formula II. They can be prepared, by a conventional method, from the corresponding aldehydes of the formula R$^2$—CHO, where R$^2$ has the above meanings, and compounds of the formula V, in which Het has the above meanings:

 (V)

The intermediates of the formula II are advantageously prepared by a method in which the starting materials are reacted in the presence or absence of a solvent or diluent and/or of a catalyst at from 20° to 200° C., preferably from 40° to 150° C. In particular, the compounds can be prepared by removing the resulting water of reaction continuously or batchwise from the reaction mixture, for example by separating it off by means of a water separator. Examples of suitable solvents are diethyl ether, chloroform, methylene chloride, toluene, xylene, tetrahydrofuran, dioxane, dimethylformamide, dimethyl sulfoxide, methanol, ethanol, isopropanol and tert.-butanol. Examples of suitable catalysts are amines, such as triethylamine, piperidine, quinuclidine and morpholine, metal hydroxides, eg. sodium hydroxide or potassium hydroxide, and metal alcoholates, eg. potassium tert.-butylate. Examples of other suitable catalysts are mineral acids, eg. sulfuric acid, organic acids, eg. formic acid, acetic acid or p-toluenesulfonic acid, salts, such as piperidinium benzoate or ammonium acetate, and amino acids, eg. β-alanine.

Depending on the reaction procedure, the intermediates of the formula II are obtained as mixtures of the geometric isomers, one of the isomers generally predominating. The pure isomers can be isolated from these mixtures by conventional purification operations, eg. crystallization, distillation or chromatography.

The novel compounds of the formula I can be prepared using, alternatively, isomer mixtures of the formula II or the corresponding pure geometric isomers.

The compounds of the formula I contain two or more chiral centers and can therefore be present in the form of enantiomer or diastereomer mixtures.

The pure isomers can be obtained either by isolation from the isomer mixtures or by selective syntheses.

The individual isomers generally have different biological actions. The present invention relates to the individual isomers as well as their mixtures.

The novel addition salts with acids are obtainable by reacting compounds of the general formula I with acids. They are generally crystalline compounds and are well tolerated by plants.

METHOD 1

Preparation of the Intermediate

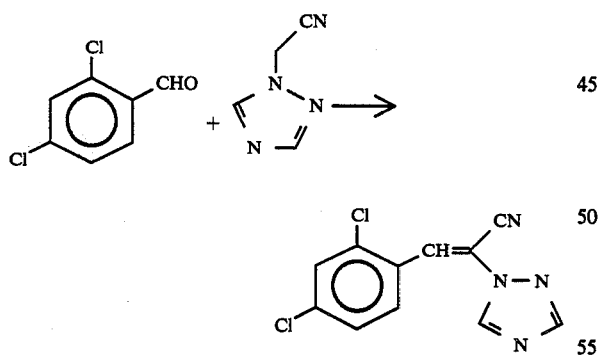

138.9 g (790 millimoles) of 2,4-dichlorobenzaldehyde, 76.7 g (710 millimoles) of 2-(1,2,4-triazol-1-yl)-acetonitrile and 1 g of piperidine in 1 l of toluene are heated at the boil under a water separator until 1 equivalent of water has been separated off. The mixture is then left to cool, and the precipitated crystals are filtered off under suction. They can be purified by recrystallization from toluene. 56.5 g (30% of theory) of 3-(2,4-dichlorophenyl)-2-(1,2,4-triazol-1-yl)-acrylonitrile of melting point 156°–160° C. are obtained.

The following intermediates can be prepared in a similar manner:

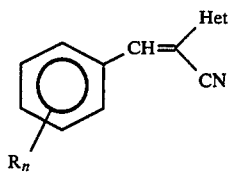

| $R_n$ | Het | Physical Data |
| --- | --- | --- |
| 4-Cl | triazole | Mp. 122–4° C. |
| 2,4-Cl$_2$ | " | Mp. 156–160° C. |
| 2-Cl | " | Mp. 130–1° C. |
| 2-F | " | Mp. 85–87° C. |
| 4-F | " | Mp. 117–20° C. |
| 4-OCH$_3$ | " | Mp. 132–6° C. |
| 4-Phenyl | " | |
| 4-CF$_3$ | " | Mp. 63° C. |
| 2-CF$_3$—4-Cl | " | |
| 2-OCH$_3$ | " | Mp. 144–147° C. |
| 2,4,6-Cl$_3$ | " | |
| 2,6-(CH$_3$)$_2$ | " | |
| 4-CH$_3$ | " | |
| 3,5-Cl$_2$ | " | |
| 3,5-(CH$_3$)$_2$ | " | |
| 2-CH$_3$ | " | |
| 2,6-Cl$_2$ | " | |
| 4-C(CH$_3$)$_3$ | " | Mp. 65° C. |
| 2,4-Cl$_2$ | imidazole | Mp. 102° C. |

The present invention embraces the pure geometric isomers of these compounds as well as their mixtures.

EXAMPLE 1

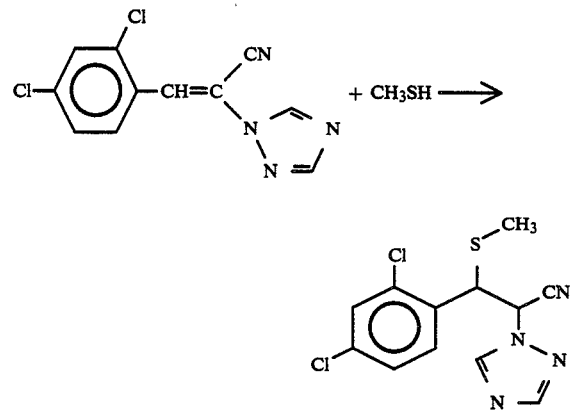

2.6 g (10 millimoles) of the nitrile obtained as described in method 1 were suspended in 20 ml of ethanol, 480 mg (10 millimoles) of methylmercaptan were added, the mixture was stirred for 14 hours at room temperature and the solvent was then evaporated under reduced pressure. The residue was chromatographed over silica gel (eluant:95:5 CH$_2$Cl$_2$/acetone) to give 2.8 g (91% of theory) of a yellowish oil (compound No. 1).

The compounds listed below can be obtained in a similar manner by appropriately choosing the starting materials and suitably adapting the process conditions.

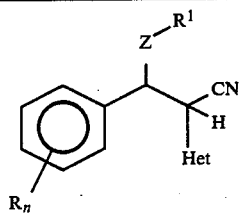

| No. | $R_n$ | Het | Z | $R^1$ | IR data [cm$^{-1}$] or m.p. [°C.] |
|---|---|---|---|---|---|
| 1 | 2,4-Cl$_2$ | 1,2,4-triazol-1-yl | S | methyl | |
| 2 | 2,4-Cl$_2$ | 1,2,4-triazol-1-yl | S | ethyl | 1505,1275,1135,676 |
| 3 | 2,4-Cl$_2$ | 1,2,4-triazol-1-yl | S | n-propyl | 2964,1504,1474,1275 |
| 4 | 2,4-Cl$_2$ | 1,2,4-triazol-1-yl | S | n-butyl | |
| 5 | 2,4-Cl$_2$ | 1,2,4-triazol-1-yl | S | n-pentyl | 2930,1505,1275,1135,676 |
| 6 | 2,4-Cl$_2$ | 1,2,4-triazol-1-yl | S | n-hexyl | 2929,1505,1275,1135 |
| 7 | 2,4-Cl$_2$ | 1,2,4-triazol-1-yl | S | n-heptyl | 2928,1505,1275,1135 |
| 8 | 2,4-Cl$_2$ | 1,2,4-triazol-1-yl | S | phenyl | 1505,1474,1276,1135 |
| 9 | 2,4-Cl$_2$ | 1,2,4-triazol-1-yl | S | 4-Cl—benzyl | oil |
| 10 | 4-F | 1,2,4-triazol-1-yl | S | methyl | |
| 11 | 4-F | 1,2,4-triazol-1-yl | S | ethyl | oil |
| 12 | 4-F | 1,2,4-triazol-1-yl | S | n-propyl | oil |
| 13 | 4-F | 1,2,4-triazol-1-yl | S | n-butyl | |
| 14 | 4-F | 1,2,4-triazol-1-yl | S | n-pentyl | 2930,1508,1276,1228 |
| 15 | 4-F | 1,2,4-triazol-1-yl | S | n-hexyl | |
| 16 | 4-F | 1,2,4-triazol-1-yl | S | n-heptyl | 2928,1508,1275,1218 |
| 17 | 4-F | 1,2,4-triazol-1-yl | S | phenyl | oil |
| 18 | 4-F | 1,2,4-triazol-1-yl | S | 4-Cl—benzyl | oil |
| 19 | 4-OCH$_3$ | 1,2,4-triazol-1-yl | S | methyl | |
| 20 | 4-OCH$_3$ | 1,2,4-triazol-1-yl | S | ethyl | |
| 21 | 4-OCH$_3$ | 1,2,4-triazol-1-yl | S | n-propyl | 2963,1513,1257,1135 |
| 22 | 4-OCH$_3$ | 1,2,4-triazol-1-yl | S | n-butyl | |
| 23 | 4-OCH$_3$ | 1,2,4-triazol-1-yl | S | n-pentyl | 2950,1510,1755,1090 |
| 24 | 4-OCH$_3$ | 1,2,4-triazol-1-yl | S | n-hexyl | m.p. 98–99 |
| 25 | 4-OCH$_3$ | 1,2,4-triazol-1-yl | S | n-heptyl | |
| 26 | 4-OCH$_3$ | 1,2,4-triazol-1-yl | S | phenyl | m.p. 125–127 |
| 27 | 4-OCH$_3$ | 1,2,4-triazol-1-yl | S | 4-Cl—benzyl | 2930,1560,1300,880 |
| 28 | 4-Cl | 1,2,4-triazol-1-yl | S | methyl | |
| 29 | 4-Cl | 1,2,4-triazol-1-yl | S | ethyl | |
| 30 | 4-Cl | 1,2,4-triazol-1-yl | S | n-propyl | 2960,1500,1270,1050 |
| 31 | 4-Cl | 1,2,4-triazol-1-yl | S | n-butyl | |
| 32 | 4-Cl | 1,2,4-triazol-1-yl | S | n-pentyl | 2950,1500,1270,1130 |
| 33 | 4-Cl | 1,2,4-triazol-1-yl | S | n-hexyl | 2920,1590,1500,1270 |
| 34 | 4-Cl | 1,2,4-triazol-1-yl | S | n-heptyl | |
| 35 | 4-Cl | 1,2,4-triazol-1-yl | S | phenyl | m.p. 130–131 |
| 36 | 4-Cl | 1,2,4-triazol-1-yl | S | 4-Cl—benzyl | |
| 37 | 2-Cl | 1,2,4-triazol-1-yl | S | methyl | |
| 38 | 2-Cl | 1,2,4-triazol-1-yl | S | ethyl | |
| 39 | 2-Cl | 1,2,4-triazol-1-yl | S | n-propyl | 1550,1480,1320,1180 |
| 40 | 2-Cl | 1,2,4-triazol-1-yl | S | n-butyl | |
| 41 | 2-Cl | 1,2,4-triazol-1-yl | S | n-pentyl | 2920,1590,1500,1270 |
| 42 | 2-Cl | 1,2,4-triazol-1-yl | S | n-hexyl | 2920,1500,1270,1180 |
| 43 | 2-Cl | 1,2,4-triazol-1-yl | S | n-heptyl | |
| 44 | 2-Cl | 1,2,4-triazol-1-yl | S | phenyl | 2960,1580,1500,1200 |
| 45 | 2-Cl | 1,2,4-triazol-1-yl | S | 4-Cl—benzyl | 2920,1500,1490,1090 |
| 46 | 3,5-Cl$_3$ | 1,2,4-triazol-1-yl | S | methyl | |
| 47 | 3,5-Cl$_3$ | 1,2,4-triazol-1-yl | S | ethyl | |
| 48 | 3,5-Cl$_3$ | 1,2,4-triazol-1-yl | S | n-propyl | |
| 49 | 3,5-Cl$_3$ | 1,2,4-triazol-1-yl | S | n-butyl | |
| 50 | 2,4-Cl$_2$ | 1,2,4-triazol-1-yl | O | methyl | m.p. 128–130 |
| 51 | 2,4-Cl$_2$ | 1,2,4-triazol-1-yl | O | ethyl | m.p. 122–123 |
| 52 | 2,4-Cl$_2$ | 1,2,4-triazol-1-yl | O | n-propyl | |
| 53 | 2,4-Cl$_2$ | 1,2,4-triazol-1-yl | O | n-butyl | |
| 54 | 2,4-Cl$_2$ | 1,2,4-triazol-1-yl | O | n-pentyl | |
| 55 | 2,4-Cl$_2$ | 1,2,4-triazol-1-yl | O | n-hexyl | |
| 56 | 2,4-Cl$_2$ | 1,2,4-triazol-1-yl | O | n-heptyl | |
| 57 | 2,4-Cl$_2$ | 1,2,4-triazol-1-yl | O | phenyl | |
| 58 | 2,4-Cl$_2$ | 1,2,4-triazol-1-yl | O | 4-Cl—benzyl | |
| 59 | 2-F | 1,2,4-triazol-1-yl | O | methyl | |
| 60 | 2-F | 1,2,4-triazol-1-yl | O | ethyl | |
| 61 | 2-F | 1,2,4-triazol-1-yl | O | n-propyl | |
| 62 | 2-F | 1,2,4-triazol-1-yl | O | n-butyl | |
| 63 | 2-F | 1,2,4-triazol-1-yl | O | n-pentyl | |
| 64 | 2-F | 1,2,4-triazol-1-yl | O | n-hexyl | |
| 65 | 2-F | 1,2,4-triazol-1-yl | O | n-heptyl | |
| 66 | 2-F | 1,2,4-triazol-1-yl | O | phenyl | |
| 67 | 2-F | 1,2,4-triazol-1-yl | O | 4-Cl—benzyl | |
| 68 | 2-F | 1,2,4-triazol-1-yl | CH$_2$ | methyl | |
| 69 | 2-F | 1,2,4-triazol-1-yl | CH$_2$ | ethyl | |

-continued

| | | | | |
|---|---|---|---|---|
| 70 | 2-F | 1,2,4-triazol-1-yl | CH$_2$ | n-propyl |
| 71 | 2-F | 1,2,4-triazol-1-yl | CH$_2$ | n-butyl |
| 72 | 2-F | 1,2,4-triazol-1-yl | CH$_2$ | n-pentyl |
| 73 | 2-F | 1,2,4-triazol-1-yl | CH$_2$ | n-hexyl |
| 74 | 2-F | 1,2,4-triazol-1-yl | CH$_2$ | n-heptyl |
| 75 | 2-F | 1,2,4-triazol-1-yl | CH$_2$ | phenyl |
| 76 | 2-F | 1,2,4-triazol-1-yl | CH$_2$ | 4-Cl—benzyl |
| 77 | 4-CF$_3$ | 1,2,4-triazol-1-yl | S | methyl | 1333,1164,1123,1073 |
| 78 | 4-CF$_3$ | 1,2,4-triazol-1-yl | S | ethyl | 1330,1131,1123,1071 |
| 79 | 4-CF$_3$ | 1,2,4-triazol-1-yl | S | n-propyl | 1328,1163,1128,1069 |
| 80 | 4-CF$_3$ | 1,2,4-triazol-1-yl | S | n-butyl | 1327,1163,1133,1070 |
| 81 | 4-CF$_3$ | 1,2,4-triazol-1-yl | S | n-pentyl | 1326,1168,1133,1071 |
| 82 | 4-CF$_3$ | 1,2,4-triazol-1-yl | S | n-hexyl |
| 83 | 4-CF$_3$ | 1,2,4-triazol-1-yl | S | n-heptyl |
| 84 | 4-CF$_3$ | 1,2,4-triazol-1-yl | S | phenyl | 1325,1168,1131,1070 |
| 85 | 4-CF$_3$ | 1,2,4-triazol-1-yl | S | 4-Cl—benzyl | 1328,1165,1131,1125,1069 |
| 86 | 2,4-Cl$_2$ | 1,2,4-triazol-1-yl | CH$_2$ | methyl |
| 87 | 2,4-Cl$_2$ | 1,2,4-triazol-1-yl | CH$_2$ | ethyl |
| 88 | 2,4-Cl$_2$ | 1,2,4-triazol-1-yl | CH$_2$ | n-propyl |
| 89 | 2,4-Cl$_2$ | 1,2,4-triazol-1-yl | CH$_2$ | n-butyl |
| 90 | 2,4-Cl$_2$ | 1,2,4-triazol-1-yl | CH$_2$ | n-pentyl |
| 91 | 2,4-Cl$_2$ | 1,2,4-triazol-1-yl | CH$_2$ | n-hexyl |
| 92 | 2,4-Cl$_2$ | 1,2,4-triazol-1-yl | CH$_2$ | n-heptyl |
| 93 | 2,4-Cl$_2$ | 1,2,4-triazol-1-yl | CH$_2$ | phenyl |
| 94 | 2,4-Cl$_2$ | 1,2,4-Triazol-1-yl | CH$_2$ | 4-Cl—benzyl |
| 95 | 2-Cl | 1,2,4-triazol-1-yl | CH$_2$ | methyl |
| 96 | 2-Cl | 1,2,4-triazol-1-yl | CH$_2$ | ethyl |
| 97 | 2-Cl | 1,2,4-triazol-1-yl | CH$_2$ | n-propyl |
| 98 | 2-Cl | 1,2,4-triazol-1-yl | CH$_2$ | n-butyl |
| 99 | 2-Cl | 1,2,4-triazol-1-yl | CH$_2$ | n-pentyl |
| 100 | 2-Cl | 1,2,4-triazol-1-yl | CH$_2$ | n-hexyl |
| 101 | 2-Cl | 1,2,4-triazol-1-yl | CH$_2$ | n-heptyl |
| 102 | 2-Cl | 1,2,4-triazol-1-yl | CH$_2$ | phenyl |
| 103 | 2-Cl | 1,2,4-triazol-1-yl | CH$_2$ | 4-Cl—benzyl |
| 104 | 2,4-Cl$_2$ | 1,2,4-triazol-1-yl | SO | methyl |
| 105 | 2,4-Cl$_2$ | 1,2,4-triazol-1-yl | SO | ethyl |
| 106 | 2,4-Cl$_2$ | 1,2,4-triazol-1-yl | SO | n-propyl |
| 107 | 2,4-Cl$_2$ | 1,2,4-triazol-1-yl | SO | n-butyl |
| 108 | 2,4-Cl$_2$ | 1,2,4-triazol-1-yl | SO | n-pentyl |
| 109 | 2,4-Cl$_2$ | 1,2,4-triazol-1-yl | SO | n-hexyl |
| 110 | 2,4-Cl$_2$ | 1,2,4-triazol-1-yl | SO | n-heptyl |
| 111 | 2,4-Cl$_2$ | 1,2,4-triazol-1-yl | SO | phenyl |
| 112 | 2,4-Cl$_2$ | 1,2,4-triazol-1-yl | SO | 4-Cl—benzyl |
| 113 | 2,4-Cl$_2$ | 1,2,4-triazol-1-yl | SO$_2$ | methyl |
| 114 | 2,4-Cl$_2$ | 1,2,4-triazol-1-yl | SO$_2$ | ethyl |
| 115 | 2,4-Cl$_2$ | 1,2,4-triazol-1-yl | SO$_2$ | n-propyl |
| 116 | 2,4-Cl$_2$ | 1,2,4-triazol-1-yl | SO$_2$ | n-butyl |
| 117 | 2,4-Cl$_2$ | 1,2,4-triazol-1-yl | SO$_2$ | n-pentyl |
| 118 | 2,4-Cl$_2$ | 1,2,4-triazol-1-yl | SO$_2$ | n-hexyl |
| 119 | 2,4-Cl$_2$ | 1,2,4-triazol-1-yl | SO$_2$ | n-heptyl |
| 120 | 2,4-Cl$_2$ | 1,2,4-triazol-1-yl | SO$_2$ | phenyl |
| 121 | 2,4-Cl$_2$ | 1,2,4-triazol-1-yl | SO$_2$ | 4-Cl—benzyl |
| 122 | 2,4-Cl$_2$ | 1,2,4-triazol-1-yl | NH | methyl |
| 123 | 2,4-Cl$_2$ | 1,2,4-triazol-1-yl | NH | ethyl |
| 124 | 2,4-Cl$_2$ | 1,2,4-triazol-1-yl | NH | n-propyl |
| 125 | 2,4-Cl$_2$ | 1,2,4-triazol-1-yl | NH | n-butyl |
| 126 | 2,4-Cl$_2$ | 1,2,4-triazol-1-yl | NH | n-pentyl |
| 127 | 2,4-Cl$_2$ | 1,2,4-triazol-1-yl | NH | n-hexyl |
| 128 | 2,4-Cl$_2$ | 1,2,4-triazol-1-yl | NH | n-heptyl |
| 129 | 2,4-Cl$_2$ | 1,2,4-triazol-1-yl | NH | phenyl |
| 130 | 2,4-Cl$_2$ | 1,2,4-triazol-1-yl | NH | 4-Cl—benzyl |
| 131 | 2,4-Cl$_2$ | 1,2,4-triazol-1-yl | NCH$_3$ | methyl |
| 132 | 2,4-Cl$_2$ | 1,2,4-triazol-1-yl | NCH$_3$ | ethyl |
| 133 | 2,4-Cl$_2$ | 1,2,4-triazol-1-yl | NCH$_3$ | n-propyl |
| 134 | 2,4-Cl$_2$ | 1,2,4-triazol-1-yl | NCH$_3$ | n-butyl |
| 135 | 2,4-Cl$_2$ | 1,2,4-triazol-1-yl | NCH$_3$ | n-pentyl |
| 136 | 2,4-Cl$_2$ | 1,2,4-triazol-1-yl | NCH$_3$ | n-hexyl |
| 137 | 2,4-Cl$_2$ | 1,2,4-triazol-1-yl | NCH$_3$ | n-heptyl |
| 138 | 2,4-Cl$_2$ | 1,2,4-triazol-1-yl | NCH$_3$ | phenyl |
| 139 | 2,4-Cl$_2$ | 1,2,4-triazol-1-yl | NCH$_3$ | 4-Cl—benzyl |
| 140 | 2,4-Cl$_2$ | imidazol-1-yl | S | methyl |
| 141 | 2,4-Cl$_2$ | imidazol-1-yl | S | ethyl |
| 142 | 2,4-Cl$_2$ | imidazol-1-yl | S | n-propyl |
| 143 | 2,4-Cl$_2$ | imidazol-1-yl | S | n-butyl |
| 144 | 2,4-Cl$_2$ | imidazol-1-yl | S | n-pentyl |
| 145 | 2,4-Cl$_2$ | imidazol-1-yl | S | n-hexyl |
| 146 | 2,4-Cl$_2$ | imidazol-1-yl | S | n-heptyl |
| 147 | 2,4-Cl$_2$ | imidazol-1-yl | S | phenyl |
| 148 | 2,4-Cl$_2$ | imidazol-1-yl | S | 4-Cl—benzyl |
| 149 | 2,4-Cl$_2$ | 3-pyridyl | S | methyl |
| 150 | 2,4-Cl$_2$ | 3-pyridyl | S | ethyl | 2930,1505,1475,1275 |
| 151 | 2,4-Cl$_2$ | 3-pyridyl | S | n-propyl |

-continued

| No. | | | | | IR data [cm$^{-1}$] or m.p. [°C.] |
|---|---|---|---|---|---|
| 152 | 2,4-Cl$_2$ | 3-pyridyl | S | n-butyl | |
| 153 | 2,4-Cl$_2$ | 3-pyridyl | S | n-hexyl | 2928,1587,1470,1476 |
| 154 | 2,4-Cl$_2$ | 3-pyridyl | S | n-heptyl | |
| 155 | 4-F | imidazol-1-yl | S | methyl | |
| 156 | 4-F | imidazol-1-yl | S | ethyl | |
| 157 | 4-F | imidazol-1-yl | S | n-propyl | |
| 158 | 4-F | imidazol-1-yl | S | n-butyl | |
| 159 | 4-F | imidazol-1-yl | S | n-pentyl | |
| 160 | 4-F | imidazol-1-yl | S | n-hexyl | |
| 161 | 4-F | imidazol-1-yl | S | n-heptyl | |
| 162 | 4-F | imidazol-1-yl | S | phenyl | |
| 163 | 4-F | imidazol-1-yl | S | 4-Cl—benzyl | |
| 164 | 4-phenyl | 1,2,4-triazol-1-yl | S | methyl | |
| 165 | 4-phenyl | 1,2,4-triazol-1-yl | S | ethyl | |
| 166 | 4-phenyl | 1,2,4-triazol-1-yl | S | n-propyl | |
| 167 | 4-phenyl | 1,2,4-triazol-1-yl | S | n-butyl | |
| 168 | 4-phenyl | 1,2,4-triazol-1-yl | S | n-pentyl | |
| 169 | 4-phenyl | 1,2,4-triazol-1-yl | S | n-hexyl | |
| 170 | 4-phenyl | 1,2,4-triazol-1-yl | S | n-heptyl | |
| 171 | 4-phenyl | 1,2,4-triazol-1-yl | S | phenyl | |
| 172 | 4-phenyl | 1,2,4-triazol-1-yl | S | 4-Cl—benzyl | |
| 173 | 2-methoxy | 1,2,4-triazol-1-yl | S | methyl | |
| 174 | 2-methoxy | 1,2,4-triazol-1-yl | S | ethyl | 1504,1495,1275,1250,1135 |
| 175 | 2-methoxy | 1,2,4-triazol-1-yl | S | n-propyl | |
| 176 | 2-methoxy | 1,2,4-triazol-1-yl | S | n-butyl | |
| 177 | 2-methoxy | 1,2,4-triazol-1-yl | S | n-pentyl | |
| 178 | 2-methoxy | 1,2,4-triazol-1-yl | S | n-hexyl | |
| 179 | 2-methoxy | 1,2,4-triazol-1-yl | S | n-heptyl | |
| 180 | 2-methoxy | 1,2,4-triazol-1-yl | S | phenyl | |
| 181 | 2-methoxy | 1,2,4-triazol-1-yl | S | 4-Cl—benzyl | |
| 182 | 4-F | 1,2,4-triazol-1-yl | | 2-F—phenyl | |
| 183 | 4-F | imidazol-1-yl | | 2-F—phenyl | |
| 184 | 2-F | 1,2,4-triazol-1-yl | | 2-F—phenyl | |
| 185 | 2-F | imidazol-1-yl | | 2-F—phenyl | |
| 186 | 2-Cl | 1,2,4-triazol-1-yl | | 2-F—phenyl | |
| 187 | 2-Cl | imidazol-1-yl | | 2-F—phenyl | |
| 188 | 4-Cl | 1,2,4-triazol-1-yl | | 2-F—phenyl | |
| 189 | 4-Cl | imidazol-1-yl | | 2-F—phenyl | |
| 190 | 4-F | 1,2,4-triazol-1-yl | | 4-F—phenyl | |
| 191 | 4-F | imidazol-1-yl | | 4-F—phenyl | |
| 192 | 2-Cl | 1,2,4-triazol-1-yl | | 4-F—phenyl | |
| 193 | 2-Cl | imidazol-1-yl | | 4-F—phenyl | |
| 194 | 4-Cl | 1,2,4-triazol-1-yl | | 4-F—phenyl | |
| 195 | 4-Cl | imidazol-1-yl | | 4-F—phenyl | |

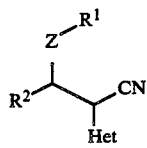

| No. | R$^2$ | Het | Z | R$^1$ | IR data [cm$^{-1}$] or m.p. [°C.] |
|---|---|---|---|---|---|
| 196 | 3-thienyl | 1,2,4-triazol-1-yl | S | methyl | |
| 197 | 3-thienyl | 1,2,4-triazol-1-yl | S | ethyl | |
| 198 | 3-thienyl | 1,2,4-triazol-1-yl | S | n-propyl | m.p. 84–88 |
| 199 | 3-thienyl | 1,2,4-triazol-1-yl | S | n-butyl | |
| 200 | 3-thienyl | 1,2,4-triazol-1-yl | S | n-pentyl | 2928,1504,1433,1275 |
| 201 | 3-thienyl | 1,2,4-triazol-1-yl | S | n-hexyl | 3110,2928,1504,1275 |
| 202 | 3-thienyl | 1,2,4-triazol-1-yl | S | n-heptyl | |
| 203 | 3-thienyl | 1,2,4-triazol-1-yl | S | phenyl | m.p. 129–132 |
| 204 | 3-thienyl | 1,2,4-triazol-1-yl | S | 4-Cl—benzyl | m.p. 103–109 |
| 205 | 3-pyridyl | 1,2,4-triazol-1-yl | S | methyl | |
| 206 | 3-pyridyl | 1,2,4-triazol-1-yl | S | ethyl | |
| 207 | 3-pyridyl | 1,2,4-triazol-1-yl | S | n-propyl | 2963,1575,1504,1275 |
| 208 | 3-pyridyl | 1,2,4-triazol-1-yl | S | n-butyl | |
| 209 | 3-pyridyl | 1,2,4-triazol-1-yl | S | n-pentyl | 2956,1504,1426,1275 |
| 210 | 3-pyridyl | 1,2,4-triazol-1-yl | S | n-hexyl | 2930,1504,1426,1275 |
| 211 | 3-pyridyl | 1,2,4-triazol-1-yl | S | n-heptyl | |
| 212 | 3-pyridyl | 1,2,4-triazol-1-yl | S | phenyl | m.p. 96–99 |
| 213 | 3-pyridyl | 1,2,4-triazol-1-yl | S | 4-Cl—benzyl | 2930,1504,1480,1275 |
| 214 | 4-pyridyl | 1,2,4-triazol-1-yl | S | methyl | |
| 215 | 4-pyridyl | 1,2,4-triazol-1-yl | S | ethyl | |
| 216 | 4-pyridyl | 1,2,4-triazol-1-yl | S | n-propyl | |
| 217 | 4-pyridyl | 1,2,4-triazol-1-yl | S | n-butyl | |
| 218 | 4-pyridyl | 1,2,4-triazol-1-yl | S | n-pentyl | |
| 219 | 4-pyridyl | 1,2,4-triazol-1-yl | S | n-hexyl | |
| 220 | 4-pyridyl | 1,2,4-triazol-1-yl | S | n-heptyl | |
| 221 | 4-pyridyl | 1,2,4-triazol-1-yl | S | phenyl | |
| 222 | 4-pyridyl | 1,2,4-triazol-1-yl | S | 4-Cl—benzyl | |

| | | | | -continued | |
|---|---|---|---|---|---|
| 223 | 2-thienyl | 1,2,4-triazol-1-yl | S | methyl | |
| 224 | 2-thienyl | 1,2,4-triazol-1-yl | S | ethyl | |
| 225 | 2-thienyl | 1,2,4-triazol-1-yl | S | n-propyl | |
| 226 | 2-thienyl | 1,2,4-triazol-1-yl | S | n-butyl | |
| 227 | 2-thienyl | 1,2,4-triazol-1-yl | S | n-pentyl | |
| 228 | 2-thienyl | 1,2,4-triazol-1-yl | S | n-hexyl | |
| 229 | 2-thienyl | 1,2,4-triazol-1-yl | S | n-heptyl | |
| 230 | 2-thienyl | 1,2,4-triazol-1-yl | S | phenyl | |
| 231 | 2-thienyl | 1,2,4-triazol-1-yl | S | 4-Cl—benzyl | |

The novel compounds have an excellent action on a broad spectrum of plant-pathogenic fungi, especially from the Ascomycetes and Basidiomycetes classes. Some of them have a systemic action and may be used as soil or foliar herbicides.

The fungicidal compounds are of particular interest for combatting a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combatting the following diseases: *Erysiphe graminis* in cereals, *Erysiphe cichoriacearum* in Cucurbitaceae, *Podosphaera leucotricha* in apples, *Uncinula necator* in graphes, *Puccinia* species in cereals, *Rhizoctonia solani* in cotton, *Ustilago* species in cereals and sugarcane, *Venturia inaequalis* (scab) in apples, *Septoria nodorum* in wheat, *Botrytis cinerea* in strawberries and grapes, *Cercospora musae* in bananas, *Pseudocercosporella herpotrichoides* in wheat and barley, *Pyricularia oryzae* in rice, *Hemileia vastatrix* in coffee, *Alternaria solani* in potatoes and tomatoes, *Plasmopara viticola* in grapes, and *Fusarium* and *Verticillium* species in various plants.

The novel compounds are used as fungicides by spraying or dusting the plants with the active ingredients, or treating the seed of plants with the active ingredients. Application may be effected before or after infection of the plants or seed by the fungi.

The compounds according to the invention may be converted into the usual formulations, e.g. solutions, emulsions, suspensions, dusts, powders, pastes and granules. The forms of application depend entirely on the purpose for which the agents are being used; they should at all events ensure a fine and uniform distribution of the active ingredient. The formulations are prepared in conventional manner, e.g., by extending the active ingredient with solvents and/or carriers, if desired using emulsifiers and dispersants. Where water is used as diluent, other organic solvents may also be employed as auxiliary solvents. Suitable compounds for preparing such formulations are solvents such as aromatics (e.g., xylene, benzene), chlorinated aromatics (e.g., chlorobenzenes), paraffins (e.g., petroleum fractions), alcohols (e.g., methanol, butanol), amines (e.g., ethanolamine, dimethylformamide), and water; carriers such as natural rock flours (e.g., kaolins, diatomaceous earth, talc, chalk) and synthetic rock flours (e.g., highly disperse silicic acid, silicates); emulsifiers such as nonionic and anionic emulsifying agents (e.g. polyoxyethylene-fatty alcohol ethers, alkyl sulfonates and aryl sulfonates); and dispersants such as lignin, sulfite waste liquors and methyl cellulose.

The formulations generally contain from 0.1 to 95, and preferably from 0.5 to 90, wt% of active ingredient.

The application rates depend on the effect desired, and range from 0.02 to 3 kg of active ingredient per hectare, or more. The novel compounds may also be used for protecting materials, e.g., for combatting wood-destroying fungi such as *Coniophora puteana* and *Polystictus versicolor*. The novel active ingredients may also be employed as fungicidally effective components of oily wood preservatives for protecting wood against wood-discoloring fungi. The agents are applied by treating, e.g., impregnating or painting, the wood with them.

The formulations and the ready-to-use products made therefrom, e.g., solutions, emulsions, suspensions, powders, dusts, pastes or granules, are applied in known manner, for example by spraying, atomizing, dusting, scattering, seed-disinfecting, or watering.

Examples of such formulations are given below.

I. 90 parts by weight of compound no. 3 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 9 is dissolved in a mixture consisting of 40 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 17 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 8 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 9 is intimately mixed with 97 parts by weight of particulate kaolin. A dust is obtained containing 3% by weight of the active ingredient.

VII. 30 parts by weight of compound no. 18 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 50 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be mixed and applied with other active ingredients, e.g., herbicides, insecticides, growth regulators, other fungicides, and fertilizers. When mixed with other fungicides, the spectrum of fungicidal action is in many cases increased.

The following list of fungicides with which the active ingredients according to the invention may be combined is intended to illustrate, and not restrict, the combination possibilities:

sulfur
dithiocarbamates and derivatives thereof, such as
ferric dimethyldithiocarbamate
zinc dimethyldithiocarbamate
zinc ethylenebisthiocarbamate
manganese ethylenebisdithiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
0,0-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzene
4-(2-chlorophenylhydrazono)-3-methyl-5-isoxazolone
pyridine-2-thio-1-oxide
8-hydroxyquinoline and its copper salt 2,3-dihydro-5-carboxanilido-6-methyl-1,4-oxathiyne-4,4-dioxide
2,3-dihydro-5-carboxanilido-6-methyl-1,4-oxathiyne
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic acid anilide
N-formyl-N-morpholine-2,2,2-trichloroethylacetal
piperazine-1,4-diylbis-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-dicarboximide
2-cyano-N-(ethylaminocarbonyl)-2-(methoximino)-acetamide
1-(2-(2,4-dichlorophenyl)-pentyl)-1H-1,2,4-triazole
2,4-difluoro-alpha-(1H-1,2,4-triazole-1-yl-methyl)-benzhydryl alcohol.

In the following experiments, the prior art compound 1-[2-(2,4-dichlorophenyl)-2-(2-propenyloxy)-ethyl]-1H-imidazole (A) was used for comparison purposes.

EXPERIMENT 1

Action on Botrytis cinerea in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprayed with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results of this experiment show that for instance novel active ingredients 2, 3, 8 and 9, applied as 0.05% sprays, had a better fungicidal action (e.g., 90%) than active ingredient A (e.g., 70%).

EXPERIMENT 2

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of Plasmopara viticola. The plants were first placed for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that for instance compounds 2, 3, 8, 9, 17 and 18, applied as 0.05% sprays, had a better fungicidal action (e.g., 97%) than compound A (e.g., 70%).

EXPERIMENT 3

Action on wheat mildew

Leaves of pot-grown wheat seedlings of the "Jubilar" variety were sprayed with aqueous liquors, the solids of which consisted of 80% (by weight) of active ingredient and 20% of emulsifier, and dusted, 24 hours after the sprayed-on layer had dried, with spores of wheat mildew (Erysiphe graminis var. tritici). The plants were then placed in a greenhouse at 20° to 22° C. and 75 to 80% relative humidity. The extent of mildew spread was determined after 7 days.

The results of the experiment show that for example novel active ingredient 50, applied as a 0.006% or 0.0015% spray, had a better fungicidal action (e.g., 100%) than active ingredient A (e.g., 90%).

We claim:

1. A compound of the formula

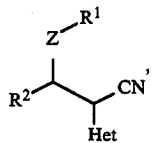

where $R^2$ is a 5-membered or 6-membered unsaturated heterocyclic structure possessing one or two hetero atoms or is phenyl which is unsubstituted or substituted by $R_n$, R is hydrogen, alkyl, alkoxy, alkylthio, alkylsulfonyl, halogen, haloalkyl, nitro, cyano, unsubstituted or halogen, cyano, nitro or halo-$C_1$-$C_2$-alkyl substituted phenyl, unsubstituted or halogen, cyano, nitro or halo-$C_1$-$C_2$-alkyl substituted phenoxy or unsubstituted or $C_1$-$C_4$-alkyl substituted amino, $R^1$ is $C_1$-$C_{10}$-alkyl, $C_3$-$C_8$-cycloalkyl, $C_4$-$C_{11}$-cycloalkyl-alkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aryl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aralkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aryloxyalkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted benzyloxyalkyl, $C_2$-$C_4$-alkenyl, propargyl, butynyl or $(CH_2-CH_2O)_m$-$R^4$, where $R^4$ is $C_1$-$C_4$-alkyl, unsubstituted or chloro-substituted aryl or unsubstituted or chloro-substituted benzyl and m is 1, 2, 3 or 4, Het is 1,2,4-triazol-1-yl or imidazol-1-yl, n is 1, 2, 3, 4 or 5, Z is oxygen, $SO_t$ or, $(R^3N)$ where t is 0, 1 or 2 and $R^3$ has the same meanings as $R^1$ and is identical to or different from $R^1$ or together with $R^1$ forms a diradical of the formula $-(CH_2)_k-X-(CH_2)_l-$, where k and l independently of one another are each 1, 2, 3, 4 or 5, and X is O, S or NH, or Z—$R^1$ is unsubstituted or alkyl, alkoxy, alkylthio, alkylsulfonyl, halogen, haloalkyl nitro or cyano substituted phenyl, or a plant-tolerated acid addition salt thereof, with the proviso that Het may also be pyrid-3-yl when Z is oxygen, $SO_t$ or $(R^3N)$ where t is 1 or 2.

2. A compound as set forth in claim 1, where $R^2$ is halophenyl, Het is triazole, Z is sulfur or oxygen, and $R^1$ is $C_1$-$C_4$-alkyl, phenyl or halobenzyl.

3. A fungicidal composition containing a solid or liquid carrier and an effective amount of a compound of the formula

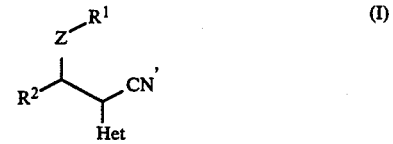

where $R^2$ is a 5-membered or 6-membered unsaturated heterocyclic structure possessing one or two hetero atoms or is phenyl which is unsubstituted or substituted by $R_n$, R is hydrogen, alkyl, alkoxy, alkylthio, alkylsulfonyl, halogen, haloalkyl, nitro, cyano, unsubstituted or halogen, cyano, nitro or halo-$C_1$-$C_2$-alkyl substituted phenyl, unsubstituted or halogen, cyano, nitro or halo-$C_1$-$C_2$-alkyl substituted phenoxy or unsubstituted or $C_1$-$C_4$-alkyl substituted amino, $R^1$ is $C_1$-$C_{10}$-alkyl, $C_3$-$C_8$-cycloalkyl, $C_4$-$C_{11}$-cycloalkyl-alkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aryl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aralkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aryloxyalkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted benzyloxyalkyl, $C_2$-$C_4$-alkenyl, propargyl, butynyl or $(CH_2-CH_2O)_m$-$R^4$, where $R^4$ is $C_1$-$C_4$-alkyl, unsubstituted or chloro-substituted aryl or unsubstituted or chloro-substituted benzyl and m is 1, 2, 3 or 4, Het is 1,2,4-triazol-1-yl or imidazol-1-yl, n is 1, 2, 3, 4 or 5, Z is oxygen, $SO_t$ or, $(R^3N)$ where t is 0, 1 or 2 and $R^3$ has the same meanings as $R^1$ and is identical to or different from $R^1$ or together with $R^1$ forms a diradical of the formula $-(CH_2)_k-X-(CH_2)_l-$, where k and l independently of one another are each 1, 2, 3, 4 or 5, and X is O, S or NH, or Z—$R^1$ is unsubstituted or alkyl, alkoxy, alkylthio, alkylsulfonyl, halogen, haloalkyl nitro or cyano substituted phenyl, or a plant-tolerated acid addition salt thereof, with the proviso that Het may also be pyrid-3-yl when Z is oxygen, $SO_t$ or $(R^3N)$ where t is 1 or 2.

4. A process for combatting fungi, wherein the fungi or the materials, plants, soil or seed to be protected against fungus attack are treated with an effective amount of a compound of the formula

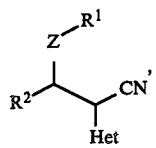

(I)

where $R^2$ is a 5-membered or 6-membered unsaturated heterocyclic structure possessing one or two hetero atoms or is phenyl which is unsubstituted or substituted by $R_n$, R is hydrogen, alkyl, alkoxy, alkylthio, alkylsulfonyl, halogen, haloalkyl, nitro, cyano, unsubstituted or halogen, cyano, nitro or halo-$C_1$-$C_2$-alkyl substituted phenyl, unsubstituted or halogen, cyano, nitro or halo-$C_1$-$C_2$-alkyl substituted phenoxy or unsubstituted or $C_1$-$C_4$-alkyl substituted amino, $R^1$ is $C_1$-$C_{10}$-alkyl, $C_3$-$C_8$-cycloalkyl, $C_4$-$C_{11}$-cycloalkyl-alkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aryl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aralkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted aryloxyalkyl, unsubstituted or halogen, cyano, nitro, $C_1$-$C_4$-alkyl, $C_1$-$C_4$-alkoxy, $C_1$-$C_4$-alkythio or halo-$C_1$-$C_4$-alkyl substituted benzyloxyalkyl, $C_2$-$C_4$-alkenyl, propargyl, butynyl or $(CH_2-CH_2O)_m-R^4$, where $R^4$ is $C_1$-$C_4$-alkyl, unsubstituted or chloro-substituted aryl or unsubstituted or chloro-substituted benzyl and m is 1, 2, 3 or 4, Het is 1,2,4-triazol-1-yl or imidazol-1-yl, n is 1, 2, 3, 4 or 5, Z is oxygen, $SO_t$ or, $(R^3N)$ where t is 0, 1 or 2 and $R^3$ has the same meanings as $R^1$ and is identical to or different from $R^1$ or together with $R^1$ forms a diradical of the formula $-(CH_2)_k-X-(CH_2)_l-$, where k and l independently of one another are each 1, 2, 3, 4 or 5, and X is O, S or NH, or Z—$R^1$ is unsubstituted or alkyl, alkoxy, alkylthio, alkylsulfonyl, halogen, haloalkyl nitro or cyano substituted phenyl, or a plant-tolerated acid addition salt thereof, with the proviso that Het may also be pyrid-3-yl when Z is oxygen, $SO_t$ or $(R^3N)$ where t is 1 or 2.

* * * * *